US00PP31720P2

(12) United States Plant Patent
Pineau

(10) Patent No.: US PP31,720 P2
(45) Date of Patent: May 5, 2020

(54) ***SCHIZOPHRAGMA* PLANT NAMED 'MINSNOW3'**

(50) Latin Name: *Schizophragma hydrangoïdes*
Varietal Denomination: MINSNOW3

(71) Applicant: Patrick Pineau, L'aunay (FR)

(72) Inventor: Patrick Pineau, L'aunay (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 16/501,152

(22) Filed: Feb. 26, 2019

(51) Int. Cl.
*A01H 5/02* (2018.01)
*A01H 6/48* (2018.01)

(52) U.S. Cl.
USPC ..... Plt./226

(58) Field of Classification Search
USPC ..... Plt./263.1, 226
See application file for complete search history.

(56) References Cited

PUBLICATIONS

UPOV-PLUTO: Plant Variety Database, Jul. 31, 2019, citation for 'minsnow3'. 1 page.*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Schizophragma* cultivar named 'MINSNOW3' is disclosed, characterized by showy white sepals, sterile flowers, blooming begins on young plants. Plants are uniquely vigorous. The new variety is a *Schizophragma*, normally produced as an outdoor garden or container plant.

2 Drawing Sheets

Latin name of the genus and species: *Schizophragma hydrangoïdes*.

Variety denomination: 'MINSNOW3'.

BACKGROUND OF THE INVENTION

The new *Schizophragma* cultivar is a product of a planned breeding program conducted by the inventor, Patrick Pineau. The objective of the breeding program was to achieve flowering on young plants. The open pollination resulting in this new variety was made during June 2006.

The seed parent is the unpatented *Schizophragma* 'Rose Sensation'. The pollen parent is unknown. The new variety was identified and selected as a potentially interesting selection Jun. 17, 2010. Selection was made at a nursery in La Menitre, France.

Asexual reproduction of the new cultivar 'MINSNOW3' was first performed Jun. 17, 2010 in La Menitre, Maine Et Loire, France, by softwood cuttings. Subsequent propagation has shown that the unique features of this cultivar are stable and reproduced true to type in 8 successive generations.

SUMMARY OF THE INVENTION

The cultivar 'MINSNOW3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSNOW3' These characteristics in combination distinguish 'MINSNOW3' as a new and distinct *Schizophragma* cultivar:

1. More vigorous plant than typical for *Schizophragma*.
2. White showy sepals.
3. Blooms occur on young plants.

PARENT COMPARISON

Plants of the new cultivar 'MINSNOW3' are similar to plants of the seed parent variety in most horticultural characteristics, however, plants of the new cultivar 'MINSNOW3' differ in the following;

1. Minsnow3 has a sepal color of white; the seed parent's sepal color is pink.

COMMERCIAL COMPARISON

Plants of the new cultivar 'MINSNOW3' can be compared to the unpatented variety *Schizophragma hydrangoïdes*, 'Windmills'. These varieties are similar in most horticultural characteristics however, 'MINSNOW3' differs in the following:

1. 'Minsnow3' is a vigorous plant, while this comparator has a medium vigor.
2. The new variety has lighter green leaves than this comparator.
3. 'Minsnow3' has sepals shaped broad deltoid, while the comparator has elongated, elliptic shaped sepals.

Plants of the new cultivar 'MINSNOW3' can also be compared to the unpatented variety *Schizophragma* 'Moonlight'. These varieties are similar in most horticultural characteristics however, 'MINSNOW3' differs in the following:

1. 'Minsnow3' is a vigorous plant, while this comparator has a medium vigor.
2. The new variety has green leaves; 'Moonlight' has blue-green leaves.

BRIEF DESCRIPTION OF THE PHOTOGRAPHS

Figure 1:
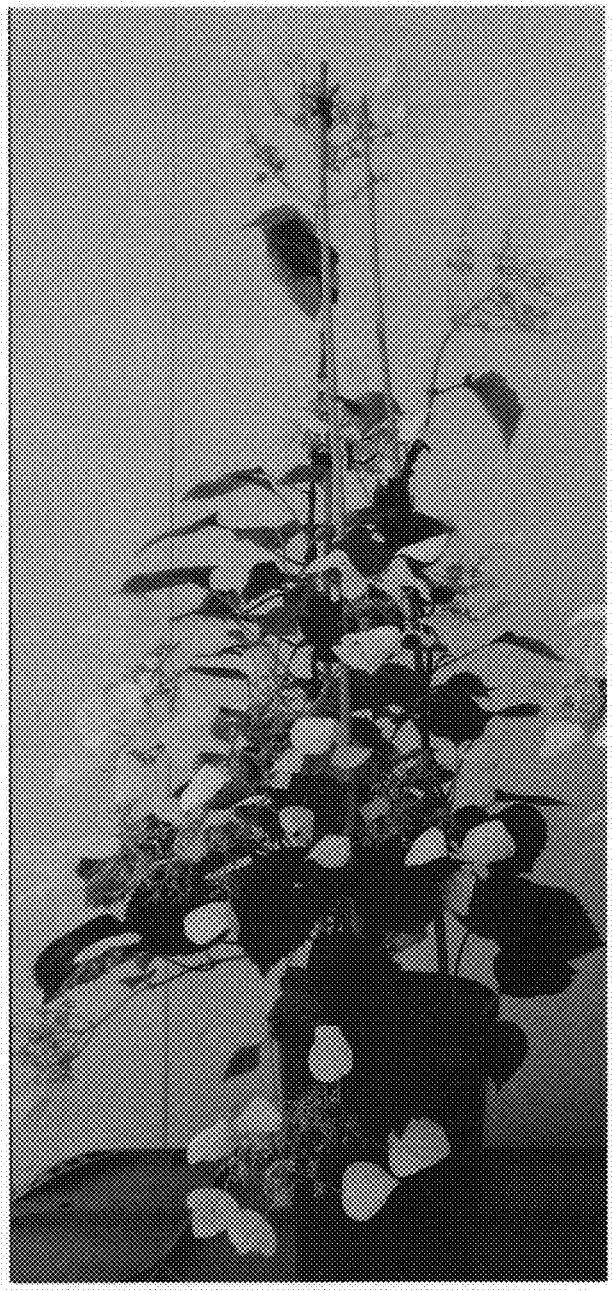

The accompanying photograph in FIG. 1 illustrates in full color a typical plant of 'MINSNOW3' grown in a 1 gallon at approximately 1 year old in La Menitre, France.

Figure 2:
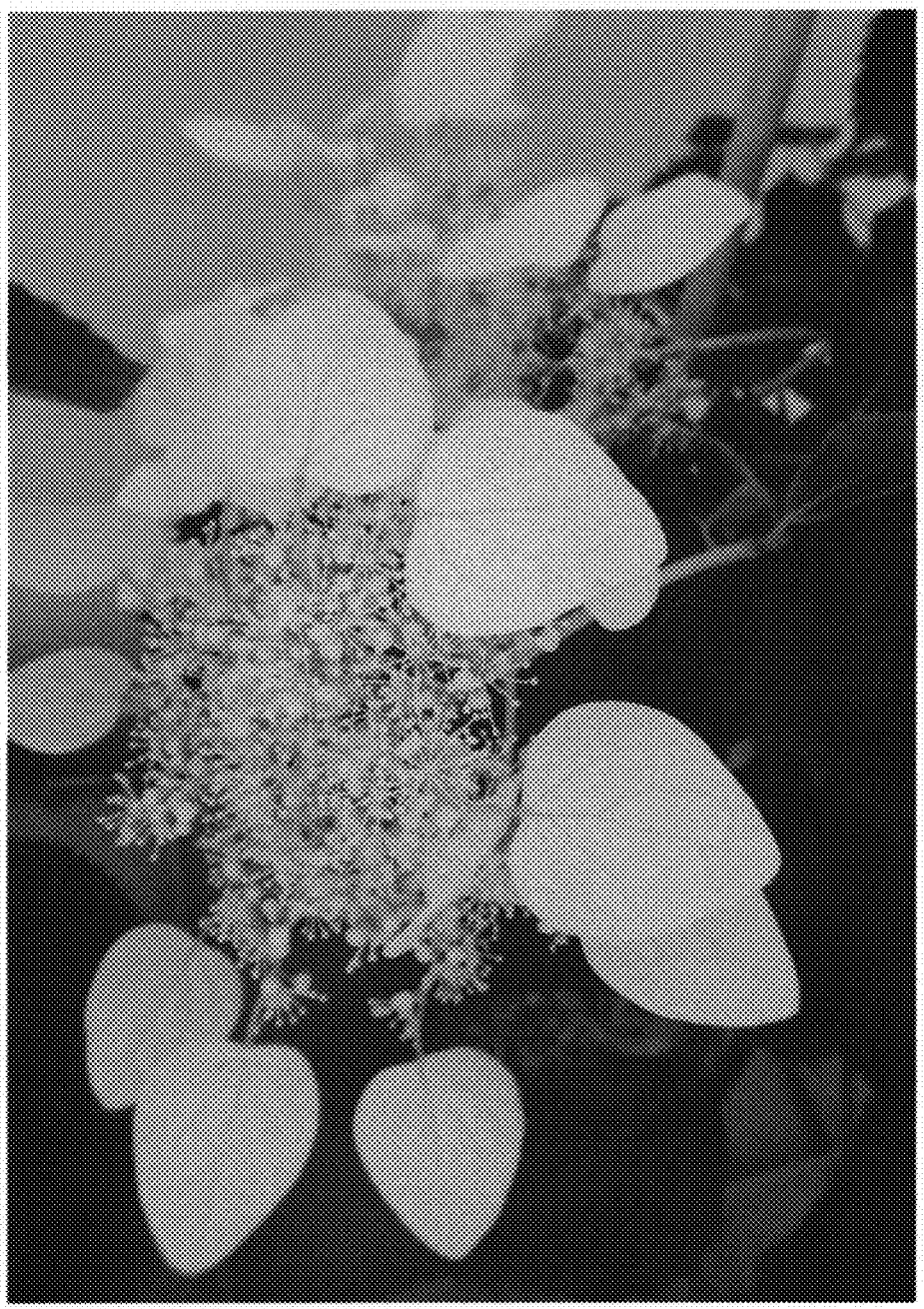

FIG. 2 illustrates in full color a typical inflorescence of 'MINSNOW3'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSNOW3' plants grown in an unheated polyhouse in Grand Haven, Mich. under natural lighting. Measurements were taken during the August of 2018. The plants were 2 to 3 years old in 2 to 3 gallon containers. The growing temperature ranged from approximately −5° C. to 27° C. Measurements and numerical values represent averages of typical plant types.

Botanical classification: *Schizophragma* 'MINSNOW3'.

PROPAGATION

Time to initiate roots: 5 weeks at approximately 20° C.

Root description: Fibrous, fleshy, medium density and thickness, freely branching. Cream/brown in color, not effectively measured with a color chart.

Time to produce a rooted young plant: 10 weeks at 20° C.

PLANT

Plant type: Perennial flowering vine.

Age of plant described: 2 to 3 years old.

Growth habit: Spreading, climbing.

Height: 77 cm, staked.

Diameter: 58 cm.

Branching habit: Horizontally oriented branches growing outward from a main stem.

Characteristics of primary lateral branches:

- *Length*.—Average 16 cm.
- *Diameter*.—Average range 1-3 cm.
- *Color*.—Young: RHS Yellow 145A. Mature: RHS Yellow 174A.
- *Strength*.—Flexible.

Internode length: 2.5 cm.

FOLIAGE

Leaf:

- *Arrangement*.—Opposite, single.
- *Average length*.—10 cm.
- *Average width*.—10 cm.
- *Shape of blade*.—Ovate.
- *Apex*.—Cuspidate.
- *Base*.—Obtuse to truncate.
- *Margin*.—Serrate.
- *Texture of top surface*.—Glabrous.
- *Texture of bottom surface*.—Glabrous.
- *Color*.—Young foliage upper side: RHS Greyed-Purple 186A. Young foliage under side: RHS Yellow-Green 144B. Mature foliage upper side: RHS Green 137A. Mature foliage under side: RHS Yellow-Green 144B.
- *Venation*.—Type: Pinnate. Venation color upper side: RHS Red 50A. Venation color under side: RHS Yellow-Green 145A.
- *Petiole*.—Length: 3.25 cm. Diameter: 3 mm. Color: RHS Yellow-Green 145A. Texture: Glabrous.

FLOWER

Natural flowering season: June-July.

Inflorescence:

- *Type*.—Corymb.
- *Height*.—7 cm.
- *Width*.—22 cm.
- *Arrangement*.—Lacecap. Terminal inflorescence made up of many small, rotate, fertile flowers sterile flowers, encircled by a smaller quantity of showy sepals.
- *Quantity*.—500 fertile flowers. 1 show sepal occurring for approximately every 10 to 15 sterile flowers.

Fertile flower:

- *Length*.—5 mm.
- *Diameter*.—5 mm.
- *Depth*.—2 mm.
- *Shape*.—Rotate.
- *Persistent or self-cleaning*.—Self-cleaning.

Bud:

- *Shape*.—Valvate.
- *Length*.—4 mm.
- *Diameter*.—4 mm.
- *Color*.—RHS White NN155A.

Petals:

- *Quantity*.—5.
- *Arrangement*.—Rotate.
- *Length*.—2 mm.
- *Width*.—2 mm.
- *Shape*.—Ovate.
- *Apex*.—Obtuse.
- *Base*.—Fused.
- *Margin*.—Entire.
- *Texture, upper and lower surfaces*.—Smooth.
- *Color*.—When opening, upper surface: RHS White NN155A When opening, lower surface: RHS White NN155A. Fully opened, upper surface: RHS White NN155A. Fully opened, lower surface: RHS White NN155A.

Showy sepals:

- *Quantity*.—1 per 10-15 fertile flowers.
- *Length*.—4 cm.
- *Width*.—4 cm.
- *Shape*.—Broad deltoid to reniform.
- *Apex*.—Acute.
- *Base*.—Cordate to truncate.
- *Margin*.—Entire.
- *Texture*.—Leathery, upper and lower surfaces.
- *Color, upper and under sides*.—Immature: RHS White NN155C, flushed with some Green-White 157B Mature: RHS White NN155C. Fading: RHS White NN155C with some Greyed-purple 186D at veins.

Peduncles:
*Length*.—1 mm.
*Diameter*.—Less than 1 mm.
*Angle*.—About 45°.
*Strength*.—Flexible.
*Texture*.—Glabrous.
*Color*.—RHS Green 143B.
Fragrance: None.

REPRODUCTIVE ORGANS

Stamens:
*Number*.—8.
*Filament length*.—7 mm.
*Filament color*.—RHS White NN155C.
Anthers:
*Shape*.—Globular.
*Length*.—Less than 1 mm.
*Color*.—RHS White NN155C.
*Pollen color*.—RHS White NN155C.
*Pollen amount*.—Some.
Pistil:
*Number*.—1, 5-lobed.
*Length*.—1 mm.
*Style*.—Length: 1 mm. Color: RHS White NN155C.
*Stigma*.—Shape: Oblong. Color: RHS White NN155C.
*Ovary color*.—RHS White NN155C.

OTHER CHARACTERISTICS

Fruits/seeds: Not observed to date.
Disease/pest resistance: Neither resistance nor susceptibility to normal diseases and pests of *Schizophragma* have been observed.
Temperature tolerance: Low temperature tolerance to −15° C. High temperature tolerance unknown.

What is claimed is:

1. A new and distinct cultivar of *Schizophragma* plant named 'MINSNOW3' as herein illustrated and described.

* * * * *